United States Patent
Erlich et al.

(10) Patent No.: US 9,752,189 B2
(45) Date of Patent: Sep. 5, 2017

(54) NON-INVASIVE EARLY DETECTION OF SOLID ORGAN TRANSPLANT REJECTION BY QUANTITATIVE ANALYSIS OF MIXTURES BY DEEP SEQUENCING OF HLA GENE AMPLICONS USING NEXT GENERATION SYSTEMS

(71) Applicants: Roche Molecular Systems, Pleasanton, CA (US); The Scripps Research Institute, La Jolla, CA (US)

(72) Inventors: Henry Erlich, Oakland, CA (US); Bryan Hoglund, Pleasanton, CA (US); Cherie Holcomb, Oakland, CA (US); Priscilla Moonsamy, Pleasanton, CA (US); Nick Newton, Oakland, CA (US); Melinda Rastrou, Pleasanton, CA (US); Nancy Schoenbrunner, Moraga, CA (US); Alison Tsan, Danville, CA (US); Daniel Salomon, La Jolla, CA (US)

(73) Assignees: Roche Molecular Systems, Inc., Pleasanton, CA (US); The Scripps Research Institute, La Jolla, CA (US)

( * ) Notice: Subject to any disclaimer, the term of this patent is extended or adjusted under 35 U.S.C. 154(b) by 541 days.

(21) Appl. No.: 14/272,752

(22) Filed: May 8, 2014

(65) Prior Publication Data

US 2014/0336056 A1 Nov. 13, 2014

Related U.S. Application Data

(60) Provisional application No. 61/821,134, filed on May 8, 2013, provisional application No. 61/894,230, filed on Oct. 22, 2013.

(51) Int. Cl.
*C12Q 1/68* (2006.01)

(52) U.S. Cl.
CPC ...... *C12Q 1/6881* (2013.01); *C12Q 2600/118* (2013.01)

(58) Field of Classification Search
None
See application file for complete search history.

(56) References Cited

U.S. PATENT DOCUMENTS

2010/0261189 A1* 10/2010 Bentley ............... C12Q 1/6869
435/6.11

FOREIGN PATENT DOCUMENTS

EP 2014059339 5/2014
WO PCTEP2014059339 5/2014

OTHER PUBLICATIONS

Gadi et al (Clinical Chemistry. 2006. 52(3):379.*
Bentley, G., et al., 2009, "High-Resolution, High Throughput HLA Genotyping by Next Generation Sequencing", Tissue Antigens 74 (5): 393-403.
Gadi, Vijayakrishna K., et al., 2006, Soluble Donor DNA Concentrations in Recipient Serum Correlate with Pancrease-Kidney Rejection, Clinical Chemistry 52 (3): 379-382 (Double-Cited).
Lambert, Nathalie C., et al., 2004, "Quantification of Maternal Michrochimerism by HLA-Specific Real-Time Polymerase Chain Reaction", Arthritis & Rheumatism 50 (3): 906-914.
Pucholt, V., et al., 1980, "Location of the Gene for 21-Hydroxylase Deficiency", Journal of Medicine Genetics,17 (6): 447-452.
Hartono et al., (2011) Non-invasive Diagnosis of Acute Rejection of Renal Allografts. Curr Opin Organ Transplant 15:35 pp. 35-41.
Morelra et al., (2009) Cell-free DNA as non-invasive acute rejection marker in renal transplantation. Clin. Chem. 55:11 pp. 1958-1966.
Snyder et al., (2011) Universal noninvasive detection of solid organ transplant rejection. PNAS 108:6229 pp. 6229-6234.
Gadi et al., (2006) Soluble donor DNA concentrations in recipient's serum correlate with pancreas-kidney rejection. Clin. Chem. 52:3 pp. 379-382.
Baxter-Lowe, L., and Busch, M., (2006) Tracking Microchimeric DNA in Plasma to Diagnose and Manage Organ Transplant Rejection Clin Chem 52:4 pp. 559-561.

* cited by examiner

*Primary Examiner* — Juliet Switzer
(74) *Attorney, Agent, or Firm* — Olga Kay

(57) ABSTRACT

The invention is a method of detecting or assessing solid organ graft (transplant) rejection by detecting donor-specific HLA alleles in a blood sample of a graft (transplant) recipient. The invention further comprises a method of detecting the presence of maternal cells in a blood sample of an offspring.

6 Claims, No Drawings

SEQUENCE LISTING

<160> NUMBER OF SEQ ID NOS: 11

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctgcaggag agtggcgcct ccgctcat                                        28

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acggagctgg ggcggcc                                                    17

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagagtggcg cctccgctca t                                               21

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aggatccccg cagaggattt cgtgtacca                                       29

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tccccgcaga ggatttcgtg tacca                                           25

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttccgggcgg tgacgga                                                    17

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
cggatccggc ccaaagccct cactc                                         25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
ccggcccaaa gccctcactc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
agctccgtca ccgcccggaa                                               20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
cggtacacct ccacgtcgct gtcsaa                                        26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
tcactcacct cggcgctgca                                               20

NON-INVASIVE EARLY DETECTION OF SOLID ORGAN TRANSPLANT REJECTION BY QUANTITATIVE ANALYSIS OF MIXTURES BY DEEP SEQUENCING OF HLA GENE AMPLICONS USING NEXT GENERATION SYSTEMS

This invention was made with government support under AI063603 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 27, 2014, is named 31598-US2_SL.txt and is 3,082 bytes in size.

BACKGROUND OF THE INVENTION

Early detection of solid organ graft rejection or graft injury is a significant unmet clinical need. Biopsy-based methods have poor sensitivity and high risk of severe complications. Therefore especially attractive are non-invasive tests that do not require a biopsy of the transplanted organ. Currently, detection of serum creatinine is a non-invasive test for graft rejection or injury. However, the test is not very specific. Additionally, detectable elevation of this marker occurs relatively late in the course of graft rejection when it is often too late to save the organ.

There have been several attempts to develop a nucleic acid-based non-invasive method for detecting graft rejection. Some methods relied on signals of graft rejection such as expression of certain rejection-associated genes. See e.g., Hartono et al., (2011) *Non-invasive Diagnosis of Acute Rejection of Renal Allografts*. Curr Opin Organ Transplant 15:35. There also have been attempts to look at donor-specific nucleic acids in the recipient's blood. Those were initially limited to Y-chromosome genes detected in female recipients of male-donated organs. Morelra et al., (2009) *Cell-free DNA as non-invasive acute rejection marker in renal transplantation*. Clin. Chem. 55:11; Snyder et al., (2011) *Universal noninvasive detection of solid organ transplant rejection*. PNAS 108:6229. There were also early attempts to detect donor-specific HLA sequences in the recipient's plasma. Gadi et al., (2006) *Soluble donor DNA concentrations in recipient's serum correlate with pancreas-kidney rejection*. Clin. Chem. 52:3. However, these attempts were widely criticized as unsuccessful: predictive value of the test was poor as there was enormous variation in the signal within each group of patients. (Reviewed in Baxter-Lowe, L., and Busch, M., (2006) *Tracking Microchimeric DNA in Plasma to Diagnose and Manage Organ Transplant Rejection* Clin Chem 52:4.) To date, there is no reliable non-invasive test for early detection of graft rejection.

SUMMARY OF THE INVENTION

In one embodiment, the invention is a method of determining a solid organ graft rejection or injury by determining a fraction of donor nucleic acid in a recipient's blood sample, the method comprising: obtaining or providing a blood sample from the recipient; probing the sample for the presence of least one donor HLA allele at at least one locus; and detecting the presence and amount or absence of the donor HLA allele indicating the presence or absence of the graft rejection or injury. In variations of this embodiment, the method further comprises determining the fraction of the donor HLA allele and wherein the fraction exceeds a predetermined threshold, diagnosing graft rejection or injury. In further variations of this embodiment, the determining step comprises calculating the ratio of the quantity of the at least one donor HLA allele to the sum of quantities of all HLA alleles at the same locus detected in the sample. In yet further variations of this embodiment, the donor and recipient HLA alleles are detected at at least two loci which are in linkage disequilibrium with each other. In yet further variations of this embodiment, the donor and recipient HLA alleles are detected at at least two loci which are not in linkage disequilibrium with each other. In yet further variations of this embodiment, the at least one locus is selected from HLA-A, HLA-B, HLA-C, DRB1, DRB3, DRB4, DRB5, DQA1, DQB1, DPA1, and DPB1. In yet further variations of this embodiment, the at least one donor and recipient HLA allele comprises sequences selected from DQA1, exon 2; DQB1, exons 2 and 3; DPA1, exon 2; DBP1, exon 2; DRB1, exon 2; DRB3, exon 2; DRB4, exon 2; and DRB5, exon 2 or an intron sequence from said HLA genes or a combination of exon and intron sequences from said genes. In yet further variations of this embodiment, the step of probing for HLA alleles comprises clonal sequencing. In yet further variations of this embodiment, probing comprises amplification or detection with oligonucleotides disclosed in Table 1. In yet further variations of this embodiment, the method further comprises a target enrichment step prior to sequencing. The target enrichment step may comprise at least one round of genomic DNA amplification or target capture. The clonal sequencing may include a step of clonal amplification performed with a forward primer and reverse primer, each primer comprising an adapter sequence and an HLA-hybridizing sequence. In yet further variations of this embodiment, probing for HLA alleles comprises the steps of: amplification with a forward primer and reverse primer to obtain HLA amplicons; performing clonal sequencing to determine the sequence of the HLA amplicons; among the sequences determined above, identifying at least one recipient HLA allele and at least one donor HLA allele at the same locus; comparing the number of recipient and donor HLA sequences identified above thereby determining fraction of donor nucleic acid in the sample. At least one primer in the method above may be selected from Table 1. In yet further variations of this embodiment, the identifying step comprises computational steps of comparing the sequences at the HLA locus to an HLA sequence database; sorting the sequences into multiple bins corresponding to known HLA alleles; identifying one or two majority sequences as recipient alleles; identifying one or two most represented minority sequences as donor alleles. In yet further variations of this embodiment, the donor HLA allele and the recipient HLA allele at the same locus are detected at two, three or more loci, for example DPB1, DQB1 and DRB1. In yet further variations of this embodiment, the donor and recipient HLA alleles at two, three or more loci are simultaneously amplified in the same reaction volume by multiplex PCR.

In yet further variations of this embodiment, the HLA alleles are quantitatively detected by a method comprising: partitioning the sample into a plurality of reaction volumes, each comprising between zero and approximately five copies of the target HLA allele; assaying each reaction volume for the presence of the target HLA allele; comparing the number of reaction volumes containing the donor HLA allele to the number of reaction volumes containing the recipient HLA allele at the same locus, thereby determining fraction of the donor nucleic acid in the sample. In variations of this embodiment, the assaying comprises PCR amplification with oligonucleotides of which at least one is selected from Table 1.

In further variations of this embodiment, the method further comprises independently obtaining genotype information for donor and recipient at the at least one HLA locus.

In another embodiment, the invention is a method of monitoring a graft recipient for development of graft rejection by periodically determining the fraction of donor HLA alleles in the recipient's blood, and if an increase in the fraction of donor DNA is detected, diagnosing the patient as having or likely to develop graft rejection.

In another embodiment, the invention is a method of determining whether a graft recipient has or is likely to develop graft rejection by determining whether concentration of donor DNA in recipient's blood exceeds a threshold level, wherein the concentration of donor DNA is determined by a method comprising obtaining or providing a volume blood sample from the recipient; quantitatively detecting at least one donor HLA allele in the volume of the sample, determining the concentration of donor DNA and comparing it to the threshold, wherein if the threshold is reached or exceeded, the recipient has or is likely to develop graft rejection. In variations of this embodiment, the at least one donor HLA allele is selected from HLA-A, HLA-B, HLA-C, DRB1, DRB3, DRB4, DRB5, DQA1, DQB1, DPA1, and DPB1 allele. In further variations of this embodiment, the at least one donor HLA allele is selected from DQA1, exon2; DQB1, exons 2 and 3; DPA1, exon 2; DBP1, exon 2; DRB1, exon 2; DRB3, exon 2; DRB4, exon 2; and DRB5, exon 2 or a combination of exon and intron sequences from said genes. In yet further variations of this embodiment, the donor HLA allele and the recipient HLA allele at the same locus are detected at two, three or more loci, for example DPB1, DQB1 and DRB1.

In yet another embodiment, the invention is a method of quantitatively detecting maternal cells in the blood of an SCID child, the method comprising: obtaining or providing a blood sample from the child; probing the sample for the presence of least one non-transmitted maternal HLA allele at at least one locus; quantifying the maternal allele detected in step (b) thereby quantitatively detecting maternal cells.

BRIEF DESCRIPTION OF THE DRAWINGS

None

DETAILED DESCRIPTION OF THE INVENTION

Definitions

The term "allele" refers to a sequence variant of a gene. One or more genetic differences can constitute an allele. For HLA alleles, typically, multiple genetic differences constitute an allele (i.e., most alleles differ from one another by more than one base). As used herein, a recipient allele is one of the two alleles present in the recipient (or a single allele present in a homozygous individual). An informative donor allele is the allele present in the donor but not present in the recipient.

The term "clonal" in the context of "clonal analysis" refers to separately analyzing an aggregate or population of molecules all derived from a single molecule. For example, "clonal sequencing" refers to individually sequencing each amplicon that was derived from the same molecule.

The term "deep sequencing" refers to a sequencing method wherein the target sequence is read multiple times in the single test. A single deep sequencing run is composed of a multitude of sequencing reactions run on the same target sequence and each, generating independent sequence readout.

The term "digital" in the context of "digital analysis" or "digital dilution" refers to the analysis of each of a plurality of individual molecules present in a sample. Digital dilution refers to distribution of the sample into a plurality of reaction volumes where, on average, one or fewer molecules are present in each reaction volume. In some instances, digital dilution enables a digital readout, e.g. obtaining a yes/no result from each individual molecule and tabulating the digital results obtained from a population of molecules by counting the number of clonal sequences. In cases of a large plurality of individual reaction volumes, digital dilutions with greater than one molecule per reaction volume may actually yield the greatest accuracy and precision of quantitation.

The terms "donor HLA" sequence and "donor's HLA sequence" are used interchangeably to denote an HLA sequence present in the organ donor. In the context of this invention, the donor sequence present in the organ donor but not the organ recipient is used.

The terms "recipient HLA" sequence and "recipient's HLA sequence" are used interchangeably to denote an HLA sequence present in the organ recipient. In the context of this invention, the recipient sequence present in the organ recipient but not the organ donor is used.

The term "polymorphism" refers to the condition in which two or more variants of a genomic sequence, or the encoded amino acid sequence, can be found in a population. A "single nucleotide polymorphism," (SNP) is a polymorphism where the variation in the sequence consists of a single polymorphic nucleotide position in the genomic sequence.

The term "genotype" refers to a combination of one or more alleles of one or more genes contained in an individual or a sample derived from the individual.

The term "haplotype" refers to a combination of one or more alleles of one or more genes present on the same chromosome of an individual.

The term "determining the genotype of an HLA gene" refers to determining the selected combination of HLA alleles in a subject. For example, in the present invention, "determining the genotype of an HLA-A gene" refers to identifying at least one of the polymorphic residues (allelic determinants) present in one or more of exons, e.g., exons 2, 3 and 4 of the HLA-A gene. In a similar fashion, genotypes of the genes HLA-B, HLA-C, DRB1, DRB3, DRB4, DRB5, DPB1, DPA1, DQA1 and DQB1 can be determined.

The term "digital droplet PCR" or "ddPCR" refers to PCR performed in a plurality of reaction volumes ("droplets") resulting from digital dilution of a sample.

The term "target region" refers to a region of a nucleic acid sequence that is to be analyzed.

The term "nucleic acid" refers to polymers of nucleotides (e.g., ribonucleotides or deoxyribo-nucleotides) both natural and non-natural. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Nucleic acids may include naturally occurring bases (adenosine, guanidine, cytosine, uracil and thymidine) as well as non-natural bases. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "primer" refers to a short nucleic acid (an oligonucleotide) that acts as a point of initiation of DNA synthesis by a nucleic acid polymerase under suitable conditions that typically include an appropriate buffer, the presence of nucleic acid precursors and one or more optional cofactors and a suitable temperature. A primer typically includes at least one target-hybridized region that is at least substantially complementary to the target sequence. This region of is typically about 15 to about 40 nucleotides in length.

The term "adapter region" or "adapter" of a primer refers to the region of a primer typically located to the 5' of the target-hybridizing region. Typically the adapter serves a function in a subsequent analysis step. For example, the adapter may hybridize to an oligonucleotide conjugated to a microparticle or other solid surface used for amplification, e.g., emulsion PCR. The adapter can also serve as a binding site for a primer used in subsequent steps, e.g., a sequencing primer. The adapter region is typically from 15 to 30 nucleotides in length.

The terms "individual identifier tag," "identification tag," "multiplex identification tag" or "MID" are used interchangeably herein to refer to a region of a primer that serves as a marker of the DNA obtained from a particular sample.

The term "amplification conditions" refers to conditions in a nucleic acid amplification reaction (e.g., PCR amplification) that allow for hybridization and template-dependent extension of the primers. The term "amplicon" refers to a nucleic acid molecule that contains all or a fragment of the target nucleic acid sequence and that is formed as the product of in vitro amplification by any suitable amplification method. Various PCR conditions are described in PCR Strategies (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990)

The term "thermostable nucleic acid polymerase" or "thermostable polymerase" refers to a polymerase enzyme, which is relatively stable at elevated temperatures when compared, for example, to polymerases from *E. coli*. A thermostable polymerase is suitable for use under temperature cycling conditions typical of the polymerase chain reaction ("PCR"). Exemplary thermostable polymerases include those from *Thermus thermophilus, Thermus caldophilus, Thermus* sp. Z05 (see, e.g., U.S. Pat. No. 5,674,738) and mutants of the *Thermus* sp. Z05 polymerase, *Thermus aquaticus, Thermus flavus, Thermus filiformis, Thermus* sp. sps17, *Deinococcus radiodurans, Hot Spring family B/clone 7, Bacillus stearothermophilus, Bacillus caldotenax, Thermotoga maritima, Thermotoga neapolitana* and *Thermosipho africanus*.

The term "sample" refers to any composition containing or presumed to contain nucleic acid from an individual. In the context of the present invention, the sample wherein the donor DNA is detected is recipient's blood and fractions derived therefrom, e.g. blood plasma. It is understood that the analysis disclosed herein is conducted on plasma samples isolated from blood, i.e., the terms "detected in patient's blood" and "detected in patient's plasma" are used interchangeably to mean that blood is obtained from the patient and plasma derived therefrom is used for the analysis. For certain aspects of the invention, e.g. for determination of donor and recipient's genotypes, any other type of body sample may be used, including without limitation, skin, plasma, serum, whole blood and blood components, saliva, urine, tears, seminal fluid, vaginal fluids and other fluids and tissues, including paraffin embedded tissues. Samples also may include constituents and components of in vitro cultures of cells obtained from an individual.

The term "valid read" in connection with nucleic acid sequencing refers to a sequence read successfully assigned (with or without error corrections) to a particular genome sequence. In reference to HLA alleles, a valid read is a sequence read successfully assigned (with or without error corrections) to one of the HLA alleles expected to be present in the sample. A read that may not be assigned to any alleles expected to be present in the sample is an invalid read.

The invention is the use of clonal analysis of nucleic acids, for example, clonal sequencing (Next Generation Sequencing (NGS) or Massively Parallel Sequencing (MPS)) or digital droplet PCR (ddPCR), or any other technique that is or will become available that comprises digital readout or clonal analysis to carry out noninvasive early detection of graft rejection or injury. It has been reported that when rejection of or injury to a transplanted solid organ occurs, DNA from the donor tissue can be found in the recipient's plasma. The invention comprises accurate quantifying of the amount and proportion of donor-specific DNA sequences in the graft recipient's plasma. A reliable test requires digital analysis of the plasma DNA because only a small fraction (a few percent or less) of the total plasma DNA is expected to be derived from the transplant even when the levels of donor DNA are elevated due to transplant rejection. The donor DNA is identified by the presence of an informative genetic marker, i.e. a marker that is polymorphic between the donor and the recipient. For example, the invention can be carried out by targeting a polymorphic gene system, such as HLA.

The invention is a method of detecting or monitoring the onset or progression of solid organ graft rejection, comprising probing the graft recipient's blood or plasma for HLA nucleic acid sequences derived from the donor, and if the donor-derived sequences are found, diagnosing graft rejection. The invention optionally comprises quantifying the amount and fraction of the donor HLA nucleic acid sequences in the recipient's blood or plasma and if the fraction is higher than the threshold determined by analysing samples derived from recipients of successful transplants, diagnosing graft rejection. The invention further comprises monitoring a patient for onset or progression of graft rejection by repeatedly probing the graft recipient's blood or plasma for HLA nucleic acid sequences derived from the donor and if the amount or fraction of the donor-derived sequences has increased, diagnosing graft rejection.

The invention provides methods of early detection of solid organ transplant rejection or injury by using unique properties of the Human Leukocyte Antigen (HLA) locus. The genes of the HLA locus (HLA genes) are the most polymorphic in the human genome. The HLA locus spans approximately 3.5 million base pairs on the short arm of chromosome 6. The major regions are the Class I and Class II regions. The Class I genes are HLA-A, HLA-B, and HLA-C and the major Class II genes are HLA-DP, HLA-DQ and HLA-DR. Polymorphisms that are expressed at the protein level are reflected in the amino acid sequence of the HLA antigen and therefore are of great interest for tissue typing for transplantation. These polymorphisms are localized primarily in exon 2 for the Class II genes and exons 2 and 3 for the Class I genes. Certain HLA loci (HLA-A, HLA-B and DR) are typically matched when possible between the donor and the recipient prior to transplantation and thus may not be useful in the context of the present invention. Other HLA loci, e.g., DP locus are typically not included in matching and therefore could be informative for a particular donor-recipient pair. The present invention enables the use of multiple HLA loci so that at least one informative locus can be found for the majority of donor-recipient pairs.

The choice of HLA locus as the target donor sequence to be detected is far superior to the targets described in the existing literature. For example, the methods that detect Y-chromosome sequences exclude gender-matched donors and all male recipients. By contrast, HLA genes are located on an autosome (chromosome 6) and thus can be detected in all gender combinations. Furthermore, HLA-based methods are superior to those targeting individual single-nucleotide differences (SNPs). Since most amplification and sequencing technologies are error-prone, perceived single-nucleotide changes are sometimes artifacts and not true SNPs. By contrast, HLA alleles differ from one another by multiple nucleotides. Thus a method comprising detection of alleles within the HLA locus is less vulnerable to error compared to a method targeting non-HLA loci. The currently available HLA genotyping methods using, e.g., clonal sequencing, enable setting the phase of multiple linked polymorphisms within an exon and make possible unambiguous determination of the sequence of each HLA allele. This feature adds an additional degree of accuracy in distinguishing donor DNA from recipient's DNA and accurately quantifying the amount of donor DNA.

The present invention is a method of diagnosing graft rejection or graft injury by detecting and quantifying the graft donor's HLA sequences among the cell-free DNA present in the graft recipient's blood or plasma. In some embodiments, the method further comprises monitoring the amount or concentration of donor DNA in the recipient's blood or plasma and if an increase has been detected, identifying the graft recipient as having or likely to develop graft rejection. In some embodiments, the invention further comprises a preliminary step or determining HLA genotype of the donor and recipient at one or more HLA loci. In some embodiment of the invention, e.g., clonal sequencing, this step is optional since the clonal sequencing method will reveal the majority HLA sequence (recipient's) and if present, the minority HLA sequence (donor's) for a polymorphic HLA locus that has not been matched between the donor and the recipient.

To ensure that an informative HLA locus is found, in some embodiments, the method comprises probing for and detecting more than one, i.e., a combination of polymorphic HLA loci. Any polymorphic HLA gene or locus or combination of loci may be used with the method of the present invention. In some embodiments, the HLA gene or gene combination is selected from HLA-A, HLA-B, HLA-C, DRB1, DRB3, DRB4, DRB5, DQA1, DQB1, DPA1, and DPB1. In some embodiments, specific exons or portions of exons (or combinations thereof) of HLA genes are targeted, e.g., DQA1: exon2; DQB1: exons 2 and 3; DPA1: exon 2; DBP1: exon 2; DRB1: exon 2, DRB3: exon 2; DRB4: exon 2; and DRB5: exon 2. In other embodiments, the polymorphic HLA gene sequence comprises introns sequences or a combination of exon and intron sequences.

The present invention comprises detection of polymorphic HLA loci in DNA present in the plasma of transplant recipients. It has been reported that much of the DNA present in human plasma is derived from cells undergoing apoptosis and is shorter or equal to about 180 base pairs. This size corresponds to a fragment of DNA wrapped around a single nucleosome. See e.g., App. Pub. No. WO2013060762, reporting that the size of DNA isolated from human plasma ranges between 85 and 230 base pairs and averages at 142 base pairs. Based on the knowledge in the art and initial experimentation, the inventors hypothesized that donor DNA present in the plasma of an organ graft recipient that was rejecting the graft may also be small. Short size of the template DNA used in the present invention presents special challenges. Because only short amplicons are possible, the number of polymorphisms that can be detected is limited. However, the inventors overcame this problem by designing suitable primers such as e.g., those listed in Table 1.

In some embodiments, multiple HLA genes or loci are analyzed in the same reaction in the form of a gene panel. In one embodiment, the panel contains HLA gene sequences that are not closely linked and not in linkage disequilibrium. This approach is especially advantageous when exact HLA genotypes of the donor and recipient have not been determined: the use of several unlinked loci assures that at least some loci will be informative (i.e., polymorphic between the donor and the recipient with an allele present in the donor that is absent in the recipient). For example, in a variation of this embodiment, sequences from genes DPB1, DQB1 and DRB1 are analyzed simultaneously. In another embodiment, the panel is formed of closely linked gene sequences that are in strong linkage disequilibrium. This approach assures that experimental errors such as a sequencing error in the recipient's sequence that creates a sequence corresponding to a known HLA allele different from the recipient's allele are recognized and discarded as "noise" rather than "signal." For example, if sequence reads from the DQA1 locus differ from the recipient's allele by one base, these could, in principle, reflect the unknown donor allele or, in contrast, a sequencing error in the recipient's allele. If these DQA1 non-recipient's sequences are, in fact, derived from the donor DNA, then one would expect, based on known linkage disequilibrium patterns, that the donor would have certain DQB1 or DRB1 alleles. If the non-recipient's DQA1 sequence is, in fact, a sequencing error, then it is extremely unlikely that an independent sequencing error in the recipient's DQB1 or DRB1 sequence would generate the expected DQB1 or DRB1 allele. This allows one to distinguish the donor allele if the donor and recipient genotypes are unknown, and distinguish the donor allele from a sequencing error in the recipient allele if the error gave rise to a sequence corresponding to a known HLA allele. One embodiment of the invention comprises detecting a combination of HLA alleles that includes two or more alleles in linkage disequilibrium with each other and at least one allele not in linkage disequilibrium with the rest. For example, in a variation of this embodiment, sequences from genes DPB1, DQB1 and DRB1 are analyzed simultaneously.

Simultaneous analysis of multiple loci can be performed in parallel reactions or by combining separate reactions in one multiplex reaction, e.g., genomic PCR wherein several amplification primers are present in the same reaction volume. In some embodiments, the method of the invention comprises a sequencing step that enables quantitative detection of the recipient and donor HLA alleles in the sample.

In this embodiment, the method takes advantage of the precision enabled by clonal analysis because only a small fraction (a few percent) of the total DNA in recipient's plasma or blood is expected to be derived from the donor.

One suitable method is "deep sequencing" by clonal sequencing also known as massively parallel sequencing (MPS) or next-generation sequencing (NGS). Next-generation sequencing methods clonally propagate in parallel millions of single DNA molecules. Each clonal population is then individually sequenced. Sometimes, NGS (MPS) methods are referred to as clonal sequencing. The advancement of the technology has allowed for ever longer sequence reads, up to 250 and more recently up to 700 nucleotides. However, cell-free DNA in the plasma of healthy individuals is present in short fragments, the majority being no more than about 150 base pairs long. (See WO2013060762) For such short target sequences, robust performance of the currently existing sequencing technology is assured.

In some embodiments, the deep sequencing step of the method of the present invention comprises an optional target enrichment step. In some embodiments, the target enrichment step comprises an amplification step. In other embodiments, other target enrichment methods are used, e.g. the library-based or probe-based methods of target enrichment described e.g., in U.S. Pat. No. 7,867,703 or 8,383,338. At least one round of amplification e.g., the first round may be performed by any method known in the art. In some embodiments, more than one round, e.g., two rounds of amplification are performed. In variations of this embodiment, subsequent rounds of amplification, e.g., amplification by PCR are performed using the same primers. In other variations of this embodiment, the primers differ by either extending further in the 3'-direction into the HLA sequence (nested primers) or by having additional sequences, e.g., non-HLA sequences, on the 5'-end.

In some embodiments, the enriched target is subjected to clonal amplification by any suitable method known in the art. In some embodiments, the clonal amplification comprises emulsion PCR described in detail in the U.S. application Ser. No. 12/245,666, filed on Oct. 3, 2008, incorporated here by reference in its entirety for all purposes. Briefly, during emulsion PCR, the amplicons from the preceding rounds of amplification are contacted with a solid phase (e.g., beads) conjugated with an oligonucleotide capable of hybridizing to the amplicon, e.g., via hybridizing to the adaptor region of the primer used in a preceding round of amplification. As a result, the bead carries annealed amplicons hybridized to the adaptor region present on the bead. The beads are then suspended in an aqueous solution and oil is added to generate an emulsion. Each bead becomes suspended in an oil-enclosed microdroplet containing all the reagents necessary to carry out the clonal round of amplification. Each microdroplet encapsulates a reaction chamber for an amplification reaction. In variations of this embodiment, two types of beads are used: one type is conjugated to an oligonucleotide capable of hybridizing to one of the two strands of the amplicon; and the second type is conjugated to an oligonucleotide capable of hybridizing to the other strand of the amplicon. In other embodiments, the clonal amplification comprises a two-dimensional surface-based (e.g., slide-based) amplification as described e.g., in U.S. Pat. Nos. 7,835,871, 8,244,479, 8,315,817 and 8,412,467. In general, any method of clonal amplification that is available or will become available is within the scope of the invention.

In some embodiments, the clonal method used to determine the presence and amount of donor DNA in a recipient's plasma sample is digital droplet PCR. Digital droplet PCR (ddPCR) enables absolute measurement of a target nucleic acid in a sample, even at very low concentrations. The ddPCR method comprises the steps of digital dilution or droplet generation, PCR amplification, detection and (optionally) analysis. The droplet generation step comprises generation of a plurality of individual reaction volumes (droplets) each containing reagents necessary to perform nucleic acid amplification. The PCR amplification step comprises subjecting the droplets (or larger reaction volumes in which droplets have been deposited) to thermocycling conditions suitable for amplification of the nucleic acid targets to generate amplicons. The detection step comprises identification of droplets (or larger reaction volumes in which droplets have been deposited) that contain and do not contain amplicons. The analysis step comprises a quantitation that yields e.g., concentration, absolute amount or relative amount (as compared to another target) of the target nucleic acid in the sample.

The ddPCR step may be performed manually (i.e., with generic devices) or with a specialized device, such as e.g., ddPCR devices available from Bio-Rad Labs. (Hercules, Calif.), or RainDance Tech. (Billerica, Mass.) or similar devices that are or will become available. In some embodiments, the entire ddPCR step is performed with a specialized device. In other embodiments, one or more steps, e.g., digital dilution, thermocycling, detection and analysis are performed with a generic device selected from e.g., a manual or automated generic pipetting device, a thermocycler, an electrophoresis device and so on.

The detection of the ddPCR product may be performed by any generic or sequence-specific means of detecting nucleic acids. The detection may take place within the reaction volume or after an additional step, such as electrophoresis or chromatography. The detection may take place during amplification (real-time PCR) or after completion of amplification (end-point PCR). A detectable label can be conjugated to a PCR reagent, such as a primer or probe. The label can be detectable by spectroscopic, photochemical, biochemical, immunochemical, chemical or other techniques can be used. To illustrate, useful labels include; radioisotopes, fluorescent dyes, electron-dense reagents, enzymes (as commonly used in ELISA), haptens, and proteins for which antisera or monoclonal antibodies are available. As an alternative to a labeled PCR reagent, the detection may be performed post-PCR with a separate labeled reagent, e.g., a sequence-specific labeled probe. Alternatively, a non-specific method of detecting nucleic acids, such as electrophoresis followed by staining can be used.

Unlike sequencing, the ddPCR-based approach disclosed herein benefits from the knowledge of which HLA loci are informative (i.e., polymorphic) between the donor and the recipient. In some embodiments, the method includes the first step of genotyping the donor and recipient to identify informative HLA loci. If such information is available, a single set of PCR reagents may be used to target the HLA locus identified as informative in the recipient's plasma sample. Alternatively, without the donor's information, the recipient's sample can be subjected to ddPCR analysis using one or more of the loci selected from HLA-A, HLA-B, HLA-C, DRB1, DRB3, DRB4, DRB5, DQA1, DQB1, DPA1, and DPB1 in the hope that at least one locus will be polymorphic between the donor and the recipient and the donor DNA will be detected.

The clonal analysis in the method of the present invention comprises the use of primers targeting (i.e., specifically hybridizing to and capable of amplifying) portions of the sequences of HLA genes HLA-A, HLA-B, HLA-C, DRB1, DRB3, DRB4, DRB5, DQA1, DQB1, DPA1, and DPB1. In some embodiments, the primers target certain exons or introns of the HLA genes, e.g., DQA1: exon2; DQB1: exons 2 and 3; DPA1: exon 2; DBP1: exon 2; DRB1: exon 2, DRB3: exon 2; DRB4: exon 2; and DRB5: exon 2. In other embodiments, the primers in a pair target a combination of exon and intron sequences. In some embodiments, one or more primers listed in Table 1 are used. As shown in Table 1, some primers are gene-specific, i.e., can amplify sequences from only one HLA gene. Other primers are generic, i.e., can amplify sequences from more than one HLA gene.

Typically, HLA primers aim to amplify and detect sequences of entire HLA exons. An average size of an HLA exon encoding the peptide binding groove is about 270 base pairs. Accordingly, a typical HLA genotyping assay involves amplicons of about 250 base pairs (Bentley, G., et al., (2009) *High resolution, high throughput HLA genotyping by next-generation sequencing*, Tissue Antigens, 74:393.) In contrast (due to the fragmented nature of DNA found in blood or plasma) the primers in the present invention aim to amplify and detect the sequence of fragments no longer than 150 base pairs. The primers used in the present invention uniquely combine the ability to amplify the short cell-free DNA with the ability to target informative (i.e. most polymorphic) regions of the HLA genes. In some embodiments, the method of the present invention is practiced with primers including at least one primer having an HLA-hybridizing region listed in Table 1.

TABLE 1

HLA-hybridizing sequences of the primers

| Locus/Exon | SEQ ID NO: | Sequence | Comment |
|---|---|---|---|
| Forward Primers | | | |
| DPB1/Exon 2 | SEQ ID NO: 1 | GCTGCAGGAGAGTG GCGCCTCCGCTCAT | Engineered restriction site |
| DPB1, DRB1, DRB3/4/5; Exon 2 | SEQ ID NO: 2 | ACGGAGCTGG GGCGGCC | |
| DPB1/Exon 2 | SEQ ID NO: 3 | GAGAGTGGCGC CTCCGCTCAT | |
| DQB1 Exon 2 | SEQ ID NO: 4 | AGGATCCCCGCAGA GGATTTCGTGTACCA | Engineered restriction site |
| DQB1 Exon 2 | SEQ ID NO: 5 | TCCCCGCAGAGGA TTTCGTGTACCA | |
| DPB1 Exon 2 | SEQ ID NO: 6 | TTCCGGGCG GTGACGGA | |
| Reverse Primers | | | |
| DPB1 Exon 2 | SEQ ID NO: 7 | CGGATCCGGCCC AAAGCCCTCACTC | Engineered restriction site |
| DPB1 Exon 2 | SEQ ID NO: 8 | CCGGCCCAAA GCCCTCACTC | |
| DPB1 Exon 2 | SEQ ID NO: 9 | AGCTCCGTCA CCGCCCGGAA | |
| DQB1 Exon 2 | SEQ ID NO: 10 | CGGTACACCTCCA CGTCGCTGTCSAA | |

TABLE 1-continued

HLA-hybridizing sequences of the primers

| Locus/Exon | SEQ ID NO: | Sequence | Comment |
|---|---|---|---|
| DPB1, DRB1, DRB3/4/5; Exon 2 | SEQ ID NO: 11 | TCACTCACCT CGGCGCTGCA | |

*S = C or G.
The primer sample contains a mixture of equal amounts of oligonucleotides containing C or G at the indicated position.

In some embodiments of the clonal sequencing, the amplicons are sequenced by a base-incorporation method, e.g. a pyrosequencing method (U.S. Pat. Nos. 6,274,320, 6,258,568 and 6,210,891); a hydrogen ion detection method (ISFET) (e.g., U.S. Pat. No. 8,262,900), or a dye-terminator detection method (U.S. Pat. Nos. 7,835,871, 8,244,479, 8,315,817 and 8,412,467.)

The HLA sequence data generated by the method of the present invention comprises HLA sequences of individual DNA molecules. A typical NGS instrument used in the method of the present invention (e.g., the GS family, 454 Life Sciences, Branford, Conn.; ION PROTON® and PGM™, Life Technologies, Grand Island, N.Y.; HISEQ® and MISEQ®, Illumina, San Diego, Calif.) contains a data analysis module capable of quantitatively detecting each sequence present in the sample, e.g., each HLA allele sequence at the same locus present in the sample. The numbers of reads corresponding to donor and recipient allele sequences are then counted to determine the presence and amount of donor allele in the sample thereby detecting graft rejection or injury.

The computational step is typically performed by a computer capable of executing the functions of a software program. The present invention may be practiced with any suitable software that is available or will become available for analysis of individual nucleic acid sequence reads generated by clonal sequencing. The software may have specific features uniquely suitable for the analysis of HLA sequences and assignment of HLA genotypes. For example, software may compare the sequence reads obtained from a sample to a database of known HLA alleles. An example of such database is the IMGT/HLA sequence database maintained at the European Molecular Biology Laboratory (EMBL), see Robinson et al. (2003) *IMGT/HLA and IMGT/MHC: sequence databases for the study of the major histocompatibility complex*, Nucleic Acids Research, 31:311. The typical software for the analysis of HLA sequence reads identifies the majority groups among the reads present in the sample. In a typical human sample, no more than four groups of sequence reads are present for each HLA sequence tested: the forward and the reverse reads for each of the two HLA alleles at the same locus. (Only two sequences will be present if the sample is derived from a homozygous individual). In the context of the present invention, the software (as pre-programmed or with the input of the user through the user interface) performs an additional function of identifying a third and possibly a fourth allele: the donor HLA alleles at the same locus present in the sample. The software (as pre-programmed or with the input of the user through the user interface) must allow the user to distinguish the minority donor alleles present at low concentration (typically between 1% and 5%) from the artifacts due to e.g., PCR misincorporations, sequencing errors, related pseudogenes, minor DNA contaminants in the sample, etc., that are generally present at a lower concentration than the donor alleles, e.g. <<0.5%.

In some embodiments, the software compares sequence reads to the HLA sequence database and identifies two (or one in case of a homozygous recipient) most prevalent sequences as recipient's alleles at a certain HLA locus. Not to limit the scope of the invention but merely by way of an example, the Conexio HLA genotyping software (Conexio Genomics, Ltd., Perth, Australia) compares the consolidated sequence reads that have been aligned with the reference sequence for a given amplicon (e.g. DQB1 exon 2) and compares the observed sequence reads with the IMGT/HLA sequence database. All the reads corresponding to that amplicon are sorted into the DQB1 exon 2 "bin" and the software assumes that there are only two allelic sequences (two forward and two reverse reads) for any one sample. These sequences are sorted into the "Master Layer" and used for the genotype assignment. All other sequence reads, typically much less abundant than the true alleles, corresponding to artifacts or contaminants, are sorted into the "Failed Layer" and are not used for genotype assignment.

The method of the present invention requires detection of more than one genotype, i.e. more than two alleles present in the sample. In some embodiments, the software (as pre-programmed or with the input of the user through a user interface) identifies and sorts the majority and minority components into multiple "bins" representing the different allelic groups corresponding to an amplicon, e.g., the DQB1 locus. For example, instead of having only one "bin" for DQB1 exon 2, the method comprises creation of multiple "bins" for multiple alleles at the DQB1 locus (e.g., DQB1*01:01, *02:01, *03:01, etc.). In some embodiments, more than 2, e.g., 3, 4, 5, 6 such bins are created. The sequences corresponding to the HLA type of the minority component are sorted into appropriate bins. Noise (i.e. PCR and sequencing errors, pseudogenes, etc.) are still, in general, sorted into the Failed Layer for each bin. This step allows quick identification of the alleles of the majority component (recipient's alleles), as well as identification of the reads corresponding to the minority component (donor's alleles). Notably, this approach is suitable for identifying donor alleles even if the donor and recipient genotype is not known. In some embodiments, the donor and recipient genotype is known. In such embodiments, the software may be modified to identify and count the specific donor and recipient alleles and discard all reads that differ therefrom as "failed" reads.

In some embodiments of the clonal sequencing, the method includes a step that minimizes errors resulting from artifacts due to e.g., PCR misincorporations, sequencing errors, related pseudogenes, minor DNA contaminants in the sample, etc. It is possible that a PCR or sequencing error could "convert" an allele into another known HLA allele. Although this event is expected to be rare, i.e., at a frequency much lower than that of the donor allele, in some embodiments, the method of the present invention includes a step of minimizing such errors. For example, the method may include analysis of two amplicons for genes that are in strong linkage disequilibrium, e.g., DQA1 and DQB1. If an error converted a majority allele into a sequence corresponding to a known non-recipient's allele for DQB1, it is extremely unlikely that a random error should also convert the recipient's DQA1 allele into a sequence corresponding to the DQA1 allele in linkage disequilibrium with the artifactual DQB1 allele.

In one embodiment, the present invention is a method of detecting graft rejection or injury by detecting and optionally quantifying donor HLA nucleic acid in a recipient's blood or plasma sample. The invention further comprises monitoring (i.e., detecting changes in) graft rejection by quantifying or quantitatively detecting donor HLA nucleic acid in the recipient's blood or plasma sample and, if increase in the donor nucleic acid is detected, diagnosing onset or progression of graft rejection. The method optionally comprises quantitatively detecting at least one donor HLA allele, quantitatively detecting at least one recipient HLA allele at the same locus; and using the quantities of the donor and recipient alleles, determining the fraction of the donor DNA in the sample or whether the fraction of donor DNA has reached or exceeded a certain threshold, thereby detecting graft rejection. The threshold may be experimentally determined by surveying a statistically significant number of graft recipients with and without graft rejection and determining the maximum value for the fraction of donor nucleic acid in the blood or plasma of the graft recipient that correlates with successful transplant. In some embodiments, at least one HLA allele is selected from HLA-A, HLA-B, HLA-C, DRB1, DRB3, DRB4, DRB5, DQA1, DQB1, DPA1, and DPB1 allele, specifically in some embodiments, the allele comprises sequences selected from DQA1, exon2; DQB1, exons 2 and 3; DPA1, exon 2; DBP1, exon 2; DRB1, exon 2; DRB3, exon 2; DRB4, exon 2; and DRB5, exon 2, or intron sequences or a combination of exon and intron sequences from these genes. In some embodiments, the quantitative detection comprises clonal sequencing. In some embodiments, the method comprises a target enrichment step prior to sequencing. In variations of this embodiment, the enrichment is performed by DNA amplification. In other variations of this embodiment, the enrichment is performed by target capture.

If ddPCR is used, the determining step comprises calculating the ratio of the concentration of the donor HLA allele or alleles to the concentration of the recipient's HLA allele or alleles at the same locus.

Without limiting the invention to a single technology or instrument but merely by way of example, an embodiment of the method may be performed using the GS family of sequencing instruments including GS FLX®, GS FLX+®, GS FLX TITANIUM® or GS Junior® (454 Life Sciences, Branford, Conn.) as described below. Droplet digital PCR may be performed using Quanta Life instrument (Bio-Rad Labs., Hercules, Calif.) as described in examples below. Other instruments and systems that are or will become available for digital or clonal analysis of nucleic acids are also contemplated herein.

In one embodiment, the target enrichment and sequencing steps comprise: (a) in the first amplification reaction, amplifying the exons or introns of one or more HLA-A, HLA-B, HLA-C, DRB1, DRB3, DRB4, DRB5, DQA1, DQB1, DPA1, and DPB1 genes that comprise polymorphic sites using amplification primers comprising the following sequences listed in the 5'- to 3'-prime direction: an adapter sequence, and an HLA-hybridizing sequence; (b) in the second amplification reaction, performing emulsion PCR; (c) determining the sequence of each amplicon obtained in step (b) using pyrosequencing; (d) assigning the HLA alleles to the recipient or the donor by comparing the sequence of the HLA amplicons determined in step (c) to the known HLA sequences to determine which HLA alleles are present in the recipient's blood or plasma; (e) for one or more HLA alleles, quantifying the number of donor's and recipient's sequencing reads corresponding to each allele obtained in step (c); and (f) using the quantity obtained in step (e), determining the fraction of the donor DNA present in the recipient's blood or plasma by calculating a ratio of the donor reads to the recipient's reads or to the total number of reads minus the background or to the total number of reads.

In variations of this embodiment, the method comprises after step (a), pooling amplicons from multiple individuals and performing the subsequent steps (b)-(c) on a pool of amplicons from multiple individuals. In this variation, the amplification primer further comprises an individual identification tag also known as multiplex identification (MID) tag.

In other embodiments, steps (b)-(e) or equivalents thereof are performed using any available deep sequencing technology and instrument (i.e., technology and instrument capable of digital sequence readout). Without limitation, the examples of instruments include GS family of instruments (454 Life Sciences, Branford, Conn.); ION PROTON® and PGM™ (Life Technologies, Grand Island, N.Y.); HISEQ® and MISEQ® (Illumina, San Diego, Calif.) or any improvements and modifications of thereof.

In some embodiments, detecting the onset or progression of graft rejection comprises quantifying the donor nucleic acids fraction. Determining the fraction comprises comparison of the reads corresponding to at least one donor allele to the sum of all reads at the same locus or to the reads corresponding to at least one recipient's allele at the same locus obtained from the sample. For ease of understanding, the term "reads" as used herein encompasses both sequencing reads and any other clonal method (e.g. droplets in digital droplet PCR) wherein a recipient's or donor's HLA allele has been detected. In some embodiments, the comparison step comprises calculating 2x the ratio of the reads corresponding to a single donor allele to the sum of all reads at the same locus obtained from the sample. In other embodiments, the comparison step is calculating the ratio of reads corresponding to a single donor allele to the reads corresponding to a single recipient's allele at the same locus obtained from the sample. Similar ratios using one or two donor alleles and one or two recipient alleles or all alleles will be immediately apparent to one skilled in the art of genetics. For example, in one embodiment, (assuming heterozygous donor and recipient with four different alleles at the same locus) if the numbers of reads for one of the recipient alleles is R and one of donor alleles is D, the donor fraction (DF) could be determined according to Formula 1:

$$DF=D/(R+D)$$ Formula 1

In another embodiment, the reads can be broken down into the forward and reverse sequencing reads for each allele. Then the donor fraction (DF) could be determined as average of reverse and forward fractions determined according to Formula 2:

$$DF_R=D_R/(R_R+D_R) \; DF_F=D_F/(R_F+D_F)$$

$$DF=(DF_R+DF_F)/2$$ Formula 2

Any number of similar formulae using one or two of the donor alleles D (or D1, D2) and one or two of the recipient alleles R (or R1, R2) at the same locus (or a single allele in the case of a homozygous individual), can be devised by one skilled in genetics and are within the scope of the invention.

In yet another embodiment, several HLA loci can be analyzed. The reads from each locus can be used to calculate the fraction of donor DNA according to Formula 1 or Formula 2 or a similar formula and the resulting donor fraction values for each locus can be averaged to obtain an estimate of the donor fraction.

In another embodiment, the invention is a method of estimating the proportion of maternal cells in the blood of a Severe Combined Immunodeficiency (SCID) child using high throughput genotyping of the HLA class I and class II loci. In variations of this embodiment, the method comprises the use of massively-parallel sequencing (using e.g., GS family of sequencing instruments including GS FLX®, GS FLX+®, GS FLX TITANIUM® or GS Junior® (454 Life Sciences, Branford, Conn.)) and suitable software (e.g., Conexio) for high resolution and high throughput genotyping of the HLA class I and class II loci. In further variations of this embodiment, the blood of a SCID child is analyzed to estimate the proportion of maternal cells by counting HLA-C allelic sequence reads corresponding to the non-transmitted maternal allele.

EXAMPLES

Example 1: Detecting Donor DNA in Recipient's Plasma by Next Generation Sequencing Sample Collection and DNA Purification Samples were collected from human recipients of kidney grafts. The DNA was prepared as follows. Whole blood was collected in Plasma Preparation Tubes (PPT) and processed within two hours. Separation of plasma was carried out according to product insert for either BD Vacutainer® PPT™ Plasma Preparation Tube or BD Vacutainer® CPT™ Cell Preparation Tube (Becton Dickinson, Inc., Franklin Lakes, N.J.) with Sodium Citrate and then stored frozen.

DNA was prepared from plasma after thawing by centrifuging at 8000 g for 5 minutes. Supernatant was then removed and again spun for an additional 5 minutes at 16000 g. Extraction of DNA from 2 mL of plasma was performed using the Roche High Pure Viral Nucleic Acid Large Volume Kit (Roche Applied Science, Inc., Indianapolis, Ind.). DNA was eluted with approximately 34 µl of water and quantified by Quibit HS DNA kit (Molecular Probes, Inc., Eugene, Oreg.).

Deep Sequencing of Cell-Free DNA from Plasma Using 454 GS FLX® Instrument

PCR amplifications were carried out in individual 25 µl reactions with 1-10 ng of DNA template and 10 pmoles each of forward and reverse primer (Table 1), 10 mM Tris-HCl, pH 8.3, 50 mM KCl, 1.5 mM MgCl, 150 µM each of dA, dC, dG and dUTP, glycerol 10% w/v, and AmpliTaq Gold® DNA polymerase. Thermal cycling conditions were: 95° C.-10 min; 31 cycles of 95° C.-15 sec., 60° C.-45 sec, 72° C.-15 sec; 72° C.-5 mM. in an ABI GeneAmp™ PCR System 9700 (Applied Biosystems, Inc., Foster City, Calif.).

The primers for use with the GS FLX® instrument had the following arrangement in the 5'-3'-orientation: Adaptor-Key tag-MID-HLA-hybridizing sequence. The adaptor, key tag and MID sequences were designed according to the manufacturers' recommendations.

Amplicon cleanup, quantification, dilution and pooling were performed as follows. Short non-specific and primer-dimer artifact products were removed from the amplicons using the AMPURE® system (Agencourt Bioscience Corp., Beverly, Mass.), following the protocol for cleanup described in the 454 Life Sciences GS GType HLA MR and HR kits (Roche Applied Science, Indianapolis, Ind.). Aliquots of purified amplicons were further evaluated by electrophoresis on a 96 well E-GEL™ (Life Technologies, Carlsbad, Calif.). If primer dimers were observed the AMPure step was repeated and product reevaluated by E-GEL™. The purified amplicons were then quantified by QUANT-IT™ PICOGREEN™ assay (Life Technologies, Carlsbad, Calif.) on a microplate spectrofluorimeter. Eight standards spanned DNA concentrations from 0 ng/μl to 50 ng/μl. Any amplicons that could not be detected by PICOGREEN™ were assigned a concentration of 0.1 ng/μl (in order to allow a dilution calculation to be made) and carried through subsequent steps. Amplicons were diluted to $1\times10^6$ molecules/μl. Pools of amplicons were made such that all amplicons destined for sequencing on a single region of the 454 PicoTiter Plate (PTP) were pooled; pools were generated so that each amplicon would give approximately the read depth desired (generally, 40,000 reads per amplicon).

Emulsion PCR, bead recovery and pyrosequencing were performed as follows. Emulsion PCR (emPCR), enrichment of DNA containing beads, and pyrosequencing on the GS FLX® instrument (454 Life Sciences, Branford, Conn.) were carried out on a 4-region PTP as per the GS FLX TITANIUM® Series manuals: emPCR Method Manual—LibA MV (January 2010); Sequencing Method Manual (May 2010), with the following exceptions: 1) during emPCR, amplicon pools were used at 0.4-0.5 copies per bead, 2) the emPCR primer was used at a concentration of 0.5 times that specified, 3) bead enrichment was automated by use of the REMe module (Roche Applied Science, Indianapolis, Ind.) on a MultiProbe HT liquid handler (Perkin Elmer, Waltham, Mass.), and 4) for sequencing, 60% of the recommended load of enriched DNA beads was dispensed onto the PTP plate.

Sequences were consolidated using the consensus functions of 454 AVA® software. ASSIGN ATF® 454 software (v 34) (Conexio Genomics, Ltd., Perth, Australia) installed on a Microsoft Windows® based computer, was used for analysis of sequences. The software assigned the alleles to each of the sequence reads and computed the number of sequence reads corresponding to each allele. Results are shown in Table 2.

Deep Sequencing of Cell-Free DNA from Plasma Using the MiSeq® Instrument

The primers for use with the MI-SEQ® instrument had the following arrangement in the 5'-3'-orientation: MiSeq tag—454 MID sequence—HLA-hybridizing sequence. (Table 1). Amplicon preparation for MiSeq® instrument (Illumina, Inc., San Diego, Calif.) sequencing optionally includes a preamplification procedure prior to PCR amplification. Optional preamplification proceeded as follows: 25 μl reactions contained 1-10 ng of DNA template and 10 pmoles each of forward and reverse primer, 10 mM Tris-HCl, pH 8.3, 50 mM KCl, 1.5 mM MgCl, 150 μM each of dA, dC, dG and dUTP, glycerol 10% w/v, and AmpliTaq Gold® DNA polymerase. Thermal cycling conditions were: 95° C.-10 min; 4 cycles of 95° C.-15 sec., 60° C.-45 sec, 72° C.-15 sec"; 72° C.-5 min. in an ABI GeneAmp® PCR System 9700. A 4 μl aliquot from each resulting preamplified sample was introduced as the DNA template into the PCR amplification reaction. The conditions were the same as described at the beginning of the section.

Amplicon cleanup and quantification were performed per manufacturer's recommendations. Each amplicon was normalized to a concentration of 0.3 ng/μl with 10 mM Tris-HCl, pH 8.3, 0.1% Tween 20 Buffer prior to a limited PCR cycle step (95° C.-30 sec; 10 cycles at 95° C.-15 sec., 63° C.-30 sec, 72° C.-45 sec; 72° C.-5 min) to add Miseq indices and capture sequences using primers that contained from 5' to 3' the MiSeq adaptor, MiSeq index and MiSeq tag. A second amplicon cleanup, quantitation, and normalization (0.3 ng/μl) were performed before pooling and loading into the MiSeq® instrument. In the resulting sequence file, the ends of the reads were "trimmed" from the sequences using bioinformatics tools developed in-house. ASSIGN ATF® 454 software (v 34) from Conexio Genomics was used for sequence analysis.

TABLE 2

Donor alleles are detected in plasma of patients with acute graft rejection

| Patient sample | Amount of DNA in 2 ml plasma, ng | Amplicon size | Donor allele 1 | Donor allele 2 | Observed % Donor allele 1[2] | Observed % Donor allele 2 | Total sequence reads[1] |
|---|---|---|---|---|---|---|---|
| AR3 | 16.2 | 155 | DPB1*04:01 | DPB1*03:01 | 0.9% | —[3] | 41253 |
| AR3 | 16.2 | 141 | DPB1*04:01 | DPB1*03:01 | 0.8% | —[3] | 87468 |
| AR5 | 10.5 | 141 | DPB1*02:01:02 | DPB1*03:01 | 1.0% | 0[4] | 60624 |

[1]Total sequence reads is the sum of all donor and recipient alleles at the same locus
[2]Since only one of the two alleles is detected, the % donor is double the observed value
[3]Second donor allele not assayable because it is identical to one of the recipient alleles
[4]Second donor allele not detected due to sampling variation

TABLE 3

Donor alleles are detected in plasma of patients with chronic graft rejection

| Patient sample | Amount of DNA in 2 ml plasma, ng | Amplicon size | Donor allele 1 | Donor allele 2 | Observed % Donor allele 1[2] | Observed % Donor allele 2 | Total sequence reads[1] |
|---|---|---|---|---|---|---|---|
| CAN2 | 8.1 | 141 | DPB1*17:01 | DPB1*40:01 | 0.4% | 0[4] | 76201 |

[1]Total sequence reads is the sum of all donor and recipient alleles at the same locus
[2]Since only one of the two alleles is detected, the % donor is double the observed value
[4]Second donor allele not detected due to sampling variation

TABLE 4

Donor alleles are not detected in plasma of patients with successful transplants

| Patient sample | Amount of DNA in 2 ml plasma, ng | Amplicon size | Donor allele 1 | Donor allele 2 | Observed % Donor allele 1 | Observed % Donor allele 2 | Total sequence reads[1] |
|---|---|---|---|---|---|---|---|
| TX3 | 63 | 155 | DPB1*13:01 | DPB1*04:01 | 0 | —[3] | 49704 |

[1]Total sequence reads is the sum of all donor and recipient alleles at the same locus
[3]Second donor allele not assayable because it is identical to one of the recipient alleles In each case, the DPB1 locus was informative for the donor-recipient pair. The results demonstrate that donor HLA sequences are detectable in the plasma of the recipient undergoing acute or chronic graft rejection. The donor DNA is undetectable in the plasma or successful transplant recipient.

Example 2: Detecting "Donor" DNA in a Cell Line Blend Mimicking a Clinical Sample by Droplet Digital PCR The sample approximating a clinical sample was a blend of nucleic acid isolated from two cell lines that represented a mixture of recipient DNA with a small (1%) amount of donor DNA. The "recipient" cell line was EDBU and the "donor" cell line was OLGA. The mixture comprised 1% OLGA/99% EDBU. The cell lines have distinct DPB1 genotypes that can be distinguished by the two probes described below. Under experimental conditions, each probe specifically hybridizes to both alleles in the target cell line and does not hybridize to the alleles in the other cell line.

The ddPCR setup was done per manufacturer's instructions for QX100™ Droplet Generator (BioRad Labs., Hercules, Calif.). SEQ ID NOs: 6 and 8 (Table 1) were used to amplify DPB1—the HLA locus informative in the test sample. Each sample was run in duplicate reactions. 9 uL of sample was combined with BioRad Droplet PCR Supermix, 250 nM of each probe, and 900 nM of each primer, and 4 units of uracil-N-glycosylase (UNG) in a final 20 µL PCR volume. The final reaction mixture was transferred into a single well on a droplet generator chip along with 70 uL of droplet generator oil in parallel wells. Upon completion of droplet generation, 40 uL of the resulting droplets suspended in oil was transferred to a 96 well plate. Droplets were then cycled using the following thermal cycling profile: 50° C. for 5-minutes (UNG step), followed by a 10-minute heat activation step at 95° C., and 40 cycles of 94° C. (30-seconds) to 57° C. (1-minute), and a 10-minute 98° C. hold. Endpoint fluorescence for each droplet was read in both the FAM and VIC channels using the BioRad QX100™ droplet reader. The VIC probe detects both "donor" alleles while the FAM probe detects both "recipient" alleles.

Percentage of donor DNA was determined by dividing the VIC positive signals by the total signals (VIC positives+FAM positives). Detection of any donor alleles in a recipient's sample is indicative of circulating donor DNA in the recipient's bloodstream. The data in Table 5 shows the ability of this ddPCR assay to detect donor alleles in a background of recipient's DNA; as well as determination of the fraction of donor DNA in a clinical plasma sample from a graft recipient. The observed fraction of "donor" sequences was 1.04%, closely matching the expected fraction of 1%.

TABLE 5

Detecting "donor" alleles by ddPCR

| DPB1 allele source | Concentration |
|---|---|
| "recipient" EDBU | 34.4 |
| "donor" OLGA | 0.36 |

Example 3 Detecting Maternal Cells I the Blood of a SCID Child by Detecting Maternal HLA Alleles A method using 454 amplicon sequencing and Conexio software for high resolution and high throughput genotyping of the HLA class I and class II loci was used to analyze the blood of a SCID child and estimate the proportion of maternal cells by counting HLA-C allelic sequence reads corresponding to the non-transmitted maternal allele. Here we report the development of a system that allows us to quantify HLA allelic mixtures in plasma.

DNA from plasma or contrived mixtures of cell lines was amplified using primers that targeted a short region (~150 bp to amplify small DNA fragments in plasma) of HLA DPB1 or DQB1 exon 2. Amplicons were further amplified by emulsion PCR and sequenced on a 454 GS FLX or GS Junior. Sequences were examined using modified Conexio Assign ATF 454 software. This software allowed for rapid digital analysis of each DPB1 or DQB1 allele. We also analyzed mixtures using the Illumina MiSeq.

Using the modified Conexio software, minority HLA alleles in a mixture were readily identified and separated from background "noise" i.e., sequences generated by PCR or sequencing errors. In mixtures of two heterozygous cell lines, the minority HLA alleles could be detected at 0.5% with 1 ng (~140 diploid genomes) DNA input. In 3/3 plasma samples from kidney transplant recipients undergoing acute or chronic rejection, donor HLA alleles were detected at an average of 0.6% of the total of donor plus recipient alleles.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of generating sequence information from a solid organ graft recipient, the method comprising:
   (a) providing a blood sample from the recipient;
   (b) generating HLA allele sequence at the loci DPB1 Exon 2, DRB1 Exon 2, DRB3 Exon 2, DRB4 Exon 2, DRB5 Exon 2, and DOB1 Exon 2 by a method comprising:
      i. contacting nucleic acid from the blood sample with a forward primer and reverse primer that have an HLA-hybridizing sequence consisting of SEQ ID NO: 1 and 7 for DPB 1 Exon 2, a forward primer and reverse primer that have an HLA-hybridizing sequence consisting of SEQ ID NO: 2 and 11 for DRB1 Exon 2, DRB3 Exon 2, DRB4 Exon2, and DRB5 Exon 2, and a forward primer and reverse primer that have an HLA-hybridizing sequence consisting of SEQ ID NO: 4 and 10 for DQB1 Exon 2, and amplifying to produce HLA amplicons;
      ii. performing clonal sequencing to determine the sequence of the HLA amplicons obtained in step (i);

iii. among the sequences determined in step (ii), identifying at least one recipient HLA allele and at least one non-recipient HLA allele at the same locus.

2. The method of claim 1, further comprising a step of quantifying the HLA alleles identified in step (iii) and calculating a ratio of the quantity of the at least one HLA allele to the sum of quantities of all HLA alleles at the same locus detected in the sample.

3. The method of claim 1, wherein the HLA alleles identified in step (iii) include alleles for at least two loci which are in linkage disequilibrium with each other.

4. The method of claim 1, wherein the HLA alleles identified in step (iii) include alleles for at least two loci which are not in linkage disequilibrium with each other.

5. The method of claim 1, further comprising generating HLA allele sequence at the loci HLA-A, HLA-B, HLA-C, DQA1, and DPA1.

6. The method of claim 1, further comprising generating HLA allele sequence at the loci DQA1, exon 2; DQB1, exon 3; and DPA1, exon 2.

\* \* \* \* \*

UNITED STATES PATENT AND TRADEMARK OFFICE
CERTIFICATE OF CORRECTION

PATENT NO. : 9,752,189 B2
APPLICATION NO. : 14/272752
DATED : September 5, 2017
INVENTOR(S) : Erlich et al.

Page 1 of 1

It is certified that error appears in the above-identified patent and that said Letters Patent is hereby corrected as shown below:

In the Specification

Column 1, Lines 8-10, the paragraph should be changed to:
-- STATEMENT OF GOVERNMENT LICENSE RIGHTS
This invention was made with government support under grant numbers AI063603 and AI084146 awarded by the National Institutes of Health. The government has certain rights in the invention. --

Signed and Sealed this
Fourteenth Day of April, 2020

Andrei Iancu
*Director of the United States Patent and Trademark Office*